(12) United States Patent
Tu et al.

(10) Patent No.: US 11,622,760 B2
(45) Date of Patent: Apr. 11, 2023

(54) KNOTTING ASSEMBLY FOR SURGICAL SUTURE LINE

(71) Applicant: MatrixLabs Medical Co., Ltd., New Taipei (TW)

(72) Inventors: Fungchao Tu, New Taipei (TW); WenYih Wu, Taipei (TW); Kuei-Hua Chen, Kaohsiung (TW)

(73) Assignee: MatrixLabs Medical Co., Ltd., New Taipei (TW)

( * ) Notice: Subject to any disclaimer, the term of this patent is extended or adjusted under 35 U.S.C. 154(b) by 107 days.

(21) Appl. No.: 17/070,123

(22) Filed: Oct. 14, 2020

(65) Prior Publication Data

US 2022/0110626 A1 Apr. 14, 2022

(51) Int. Cl.
*A61B 17/04* (2006.01)

(52) U.S. Cl.
CPC .. *A61B 17/0469* (2013.01); *A61B 2017/0474* (2013.01)

(58) Field of Classification Search
CPC .................. A61B 2017/0474; A61B 17/0469
See application file for complete search history.

(56) References Cited

U.S. PATENT DOCUMENTS

| | | | |
|---|---|---|---|
| 2,012,776 A * | 8/1935 | Roeder | A61B 17/12013 606/139 |
| 3,106,417 A * | 10/1963 | Clow | A01K 91/04 289/17 |
| 3,131,957 A * | 5/1964 | Musto | A01K 91/04 289/17 |
| 3,752,516 A * | 8/1973 | Mumma | A01K 91/04 289/17 |
| 4,403,797 A * | 9/1983 | Ragland, Jr. | A01K 91/04 289/17 |
| 5,395,382 A * | 3/1995 | DiGiovanni | A61B 17/0469 606/139 |
| 5,405,352 A * | 4/1995 | Weston | A61B 17/0469 606/139 |
| 5,472,446 A * | 12/1995 | de la Torre | A61B 17/0469 606/139 |
| 5,573,286 A * | 11/1996 | Rogozinski | D04G 5/00 606/228 |
| 5,643,293 A * | 7/1997 | Kogasaka | A61B 17/0469 606/139 |

(Continued)

FOREIGN PATENT DOCUMENTS

| CN | 110711001 A | 1/2020 |
|---|---|---|
| CN | 111317522 A | 6/2020 |
| CN | 111466971 A | 7/2020 |

*Primary Examiner* — Phong Son H Dang
(74) *Attorney, Agent, or Firm* — Alan D. Kamrath; Karin L. Williams; Mayer & Williams PC

(57) ABSTRACT

A knotting assembly for surgical suture line has an outer tube and an inner tube being slidably mounted in the outer tube. The inner tube protrudes from the outer tube and forms a loop section between a distal end thereof and a distal end of the outer tube. A suture line is looped surround the loop section to form a pre-knot and a loop. The suture has an inner section being moveably inserted in the inner tube. The loop is inserted by at least one second suture line. While the inner section is pulled, the second loop is closed to hold the at least one second suture line and folds the second suture line and pulls the folded second suture into the inner tube to finish the knot.

9 Claims, 10 Drawing Sheets

(56) References Cited

U.S. PATENT DOCUMENTS

| | | | | |
|---|---|---|---|---|
| 5,681,331 A * | 10/1997 | de la Torre | ........ | A61B 17/0483 606/139 |
| 5,709,694 A * | 1/1998 | Greenberg | ......... | A61B 17/0483 606/147 |
| 5,716,368 A * | 2/1998 | de la Torre | ........ | A61B 17/0469 606/139 |
| 5,746,752 A * | 5/1998 | Burkhart | ............ | A61B 17/0469 606/139 |
| 5,797,928 A * | 8/1998 | Kogasaka | ........ | A61B 17/12009 606/139 |
| 5,871,490 A * | 2/1999 | Schulze | ............. | A61B 17/0625 606/139 |
| 5,893,592 A * | 4/1999 | Schulze | ............. | A61B 17/0469 606/228 |
| 7,883,518 B1 * | 2/2011 | Davies | ............... | A61B 17/0469 606/148 |
| 8,511,721 B1 * | 8/2013 | Farner | .................... | A01K 91/04 289/17 |
| 9,119,893 B2 * | 9/2015 | McDevitt | ................ | A61L 17/04 |
| 10,172,610 B2 * | 1/2019 | Fikatas | .............. | A61B 17/0469 |
| 10,542,969 B2 * | 1/2020 | Pereira | ............... | A61B 17/0469 |
| 11,039,830 B2 | 6/2021 | Piccirillo | | |
| 11,224,417 B2 * | 1/2022 | Nason | ................ | A61B 17/0401 |
| 2009/0228025 A1 * | 9/2009 | Benson | ............. | A61B 17/0469 606/144 |
| 2010/0249809 A1 * | 9/2010 | Singhatat | ........... | A61B 17/0485 606/228 |
| 2013/0237997 A1 * | 9/2013 | Arai | .................. | A61B 17/0401 606/232 |
| 2014/0074157 A1 * | 3/2014 | Hirotsuka | .......... | A61B 17/0482 606/228 |
| 2016/0302789 A1 * | 10/2016 | Hirotsuka | .......... | A61B 17/0469 |

* cited by examiner

KNOTTING ASSEMBLY FOR SURGICAL SUTURE LINE

FIELD

The present disclosure relates to a surgical knot assembly, and more particularly, the disclosure relates to a surgical knot assembly and methods of use thereof adapted for facilitating the process of suturing and knot-tying in a surgical operation for an operator such as a surgeon or a healthcare professional.

BACKGROUND

Surgical suturing typically requires a well knotted end to hold and maintain a body tissue or a treatment site together to stop bleeding and to promote healing.

However, conventional knot-tying process and techniques can be exceedingly difficult, complex and time-consuming. Therefore, there is a need to improve the conventional knot-tying process and approach.

SUMMARY OF THE DISCLOSURE

To solve the aforementioned problems, the main objective of the present disclosure is to provide a surgical knot assembly and methods of use thereof that is simple and time-saving for assisting healthcare professionals at delivering a secure surgical knot with consistent knot strength each time.

To achieve the said objectives, the present disclosure provides a surgical knot assembly for tying a surgical knot, comprising:
an outer tube; an inner tube slidably interconnected within the outer tube and having a distal end protruding from the outer tube as a neck; and a strand of suture material having a first portion of a length configured releasably engaged to the neck being a pre-tied knot, and having a second portion of a length extending from a cavity at the distal end of the inner tube, thereby forming a loop between the distal end of the inner tube and the neck to receive at least a strand of suture filament therein, wherein size of the loop is variable by manoeuvring the suture material and closing the loop as the neck retracts back into the outer tube, allowing the loop, the pre-tied knot and the suture filament to be fastened together creating a surgical knot held at the cavity.

Preferably, the cavity of the inner tube has a smaller diameter than a sum of a diameter of the loop, the pre-tied knot and the suture filament fastened together.

Preferably, the pre-tied knot is whirled around the inner tube for at least twice, wherein the suture material and at least a strand of the suture filament having a same measurement and dimension.

Preferably, at least a strand of the suture filament having at least two segments intertwining with the loop.

Preferably, the suture filament first penetrates through a body tissue or a treatment site before intertwining with the loop.

Preferably, when the assembly in use and the loop has received at least a strand of the suture filament therein readily for tightening or fastening to create a secure surgical knot, size of the loop is variable by manoeuvring the suture material from a control of the assembly. As the loop tightens, the neck retracts back into the outer tube, allowing the loop, the pre-tied knot and the suture filament to be fastened together and thereby creating a surgical knot held at the cavity.

DETAILED DESCRIPTION OF THE DISCLOSURE

Figure 1:
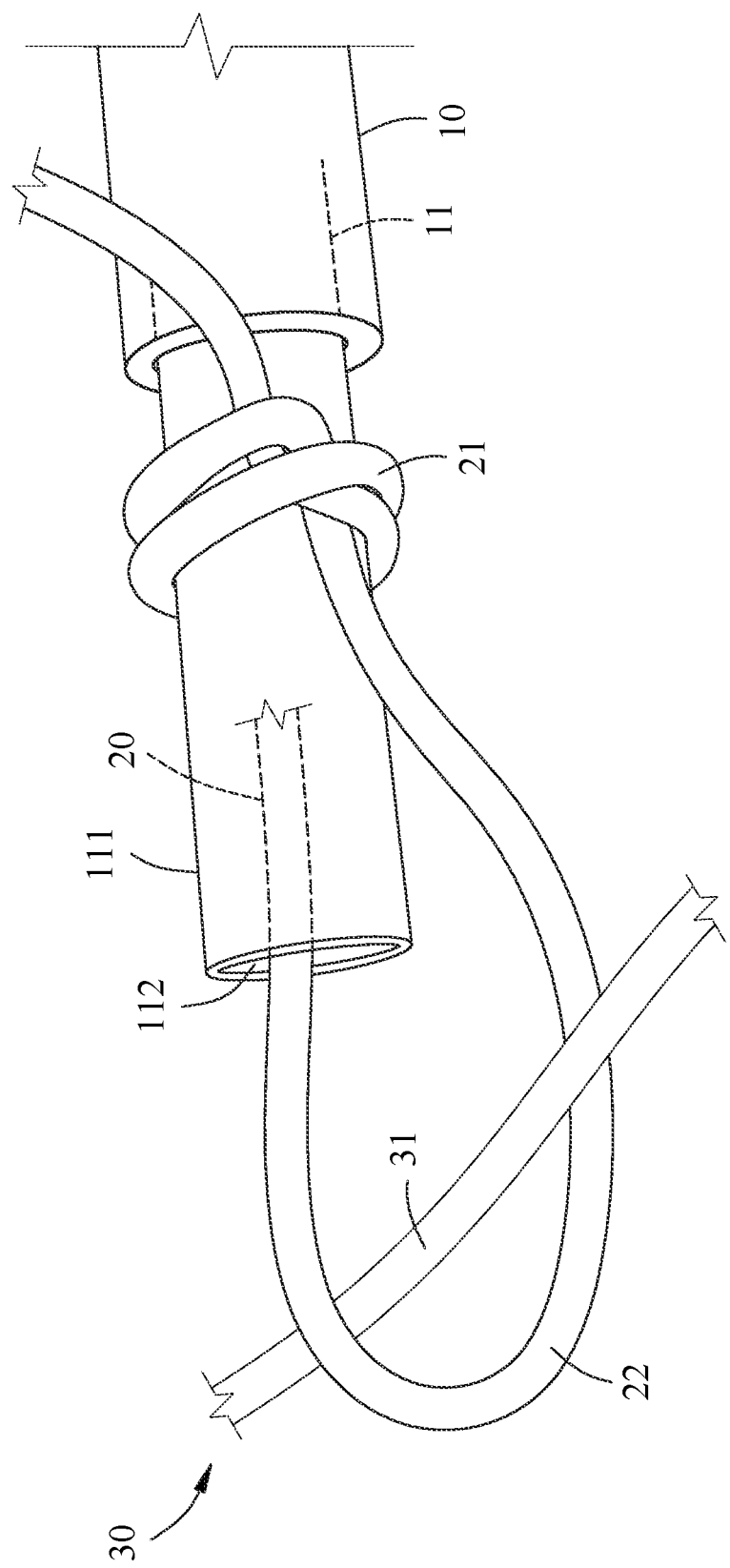
FIG. 1 is a perspective view of a first embodiment of a surgical knot assembly in accordance with the present disclosure.
Figure 2:
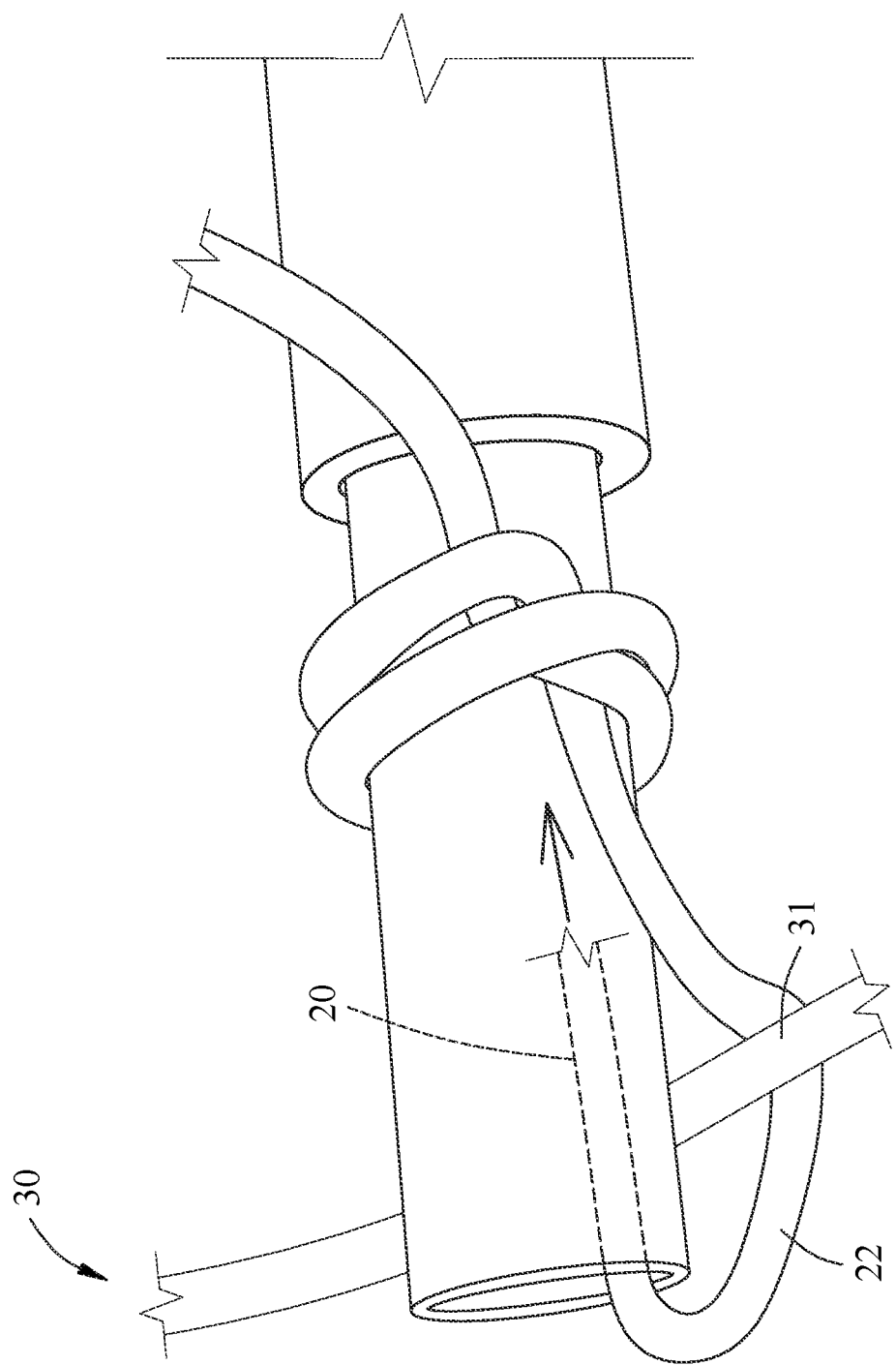
FIGS. 2 to 4 depicts the surgical knot assembly of FIG. 1 in operation.
Figure 3:
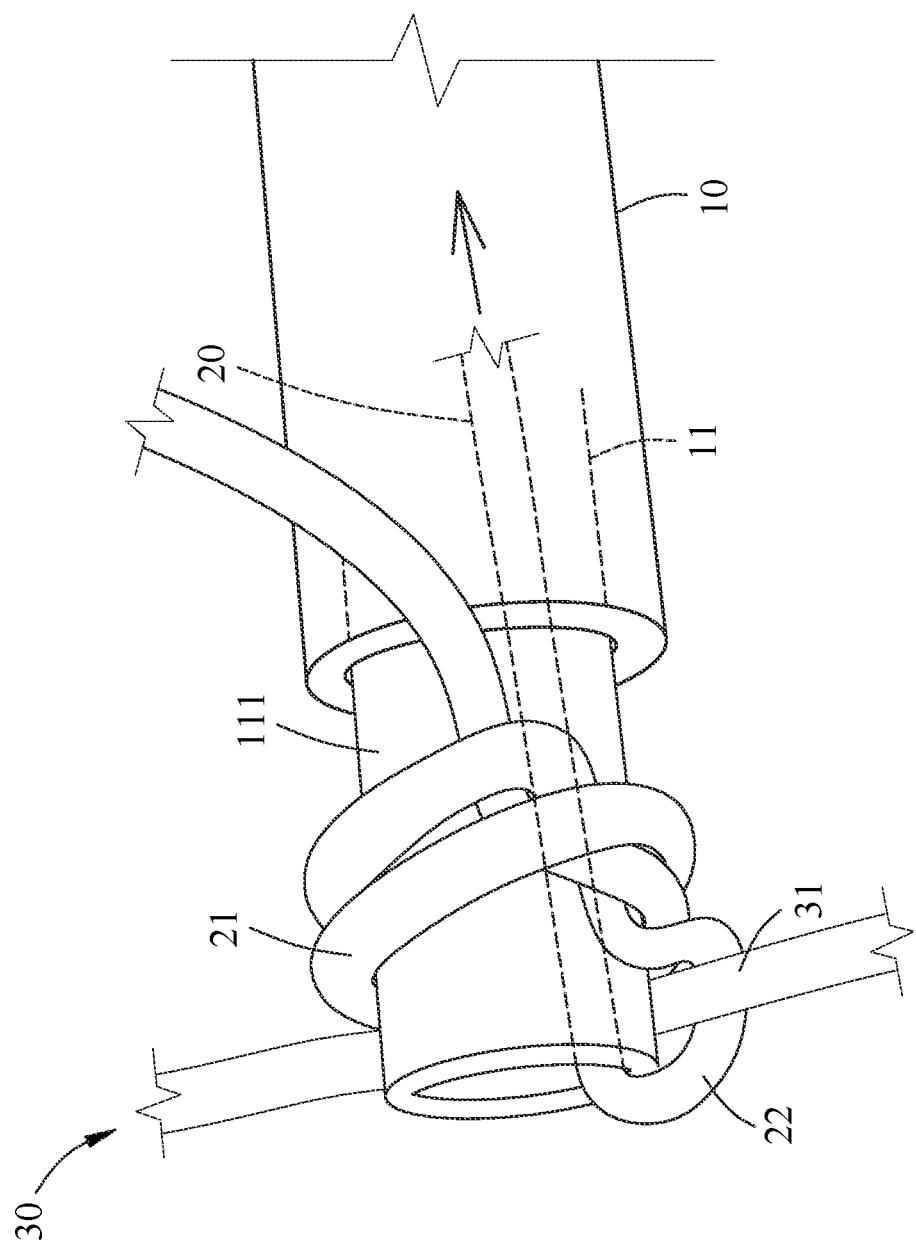

Other objectives, advantages and novel features of the present disclosure will become more apparent from the following detailed description when taken in conjunction with the accompanying drawings.

With reference to FIGS. 1 to 4, according to a preferred embodiment of the present disclosure, a surgical knot assembly for tying a surgical knot is shown. The surgical knot assembly for tying a surgical knot comprises an outer tube 10, an inner tube 11 slidably interconnected within the outer tube 10 and having a distal end protruding from the outer tube 10 as a neck 111, and a strand of suture material 20 having a first portion of a length configured releasably engaged to the neck 111 being a pre-tied knot 21, and having a second portion of a length extending from a cavity 112 at the distal end of the inner tube 11, thereby forming a loop 22 between the distal end of the inner tube 11 and the neck 111 to receive at least a strand of suture filament 30 therein. The pre-tied knot 21 can be configured and/or arranged to accommodate a particular desired strength of knot. Preferably, the pre-tied knot 21 is whirled around the inner tube 11 for at least once. With reference to the present embodiment, a two-turned slip knot is shown.

With further references to FIGS. 1 to 4, the size of the loop 22 is variable by manoeuvring the suture material 20 and closing the loop 22 as the neck 111 retracts into the outer tube 10, allowing the loop 22, the pre-tied knot 21 and the suture filament 30 to be fastened together creating a surgical knot A held at the cavity 112. The suture material 20 can be manoeuvred via a control of the assembly. In certain embodiments, the diameters of the suture material 20 and suture filament 30 have the same and/or close diameter measurements to ensure the efficiency, robustness, and security of the surgical knot.

In some embodiments, the dimensions and/or specification of the suture material 20 and suture filament 30 are vastly different. Therefore, as the surgical knot assembly is readily detachable from each other, the operator can replace parts of the assembly and/or choose and apply the applicable configuration thereof as required.

Figure 4:
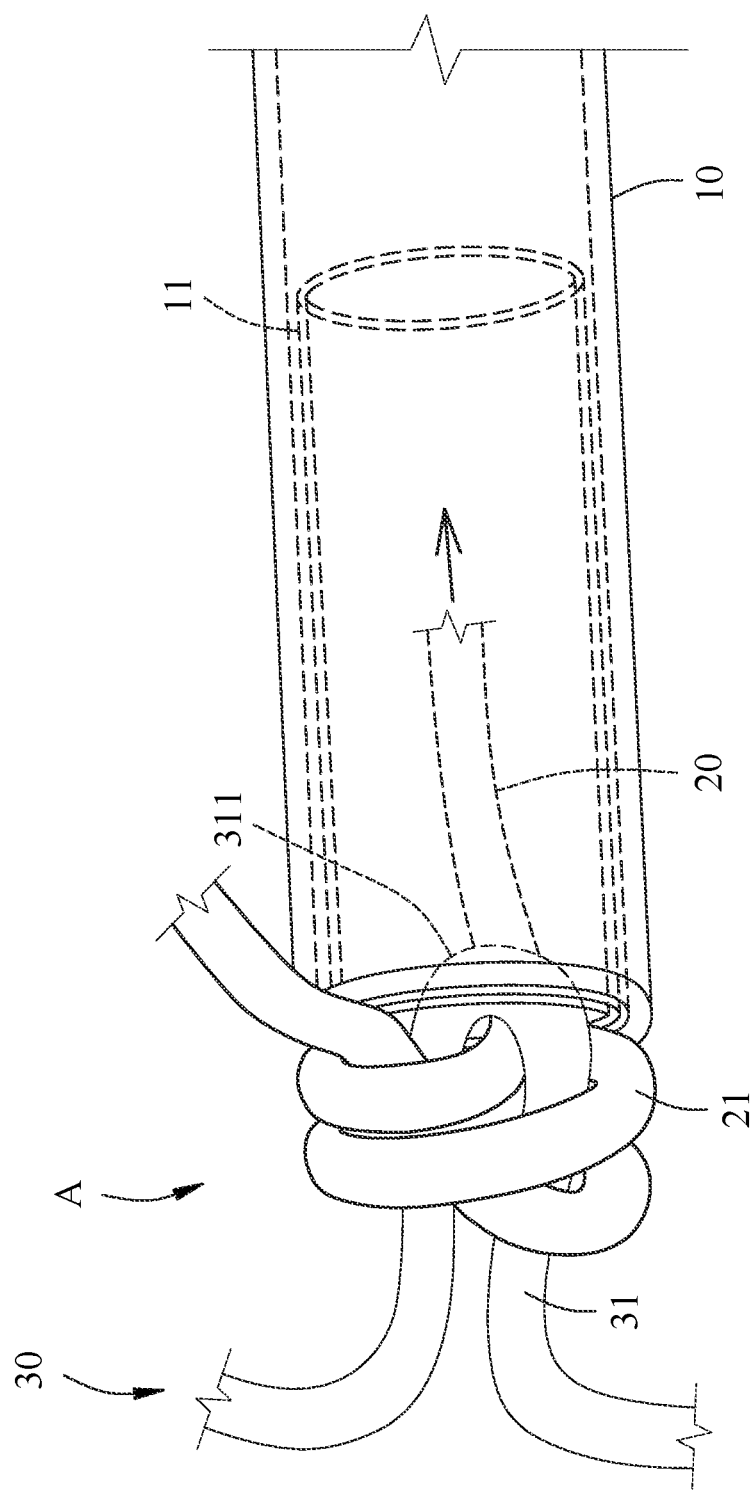
Figure 5:
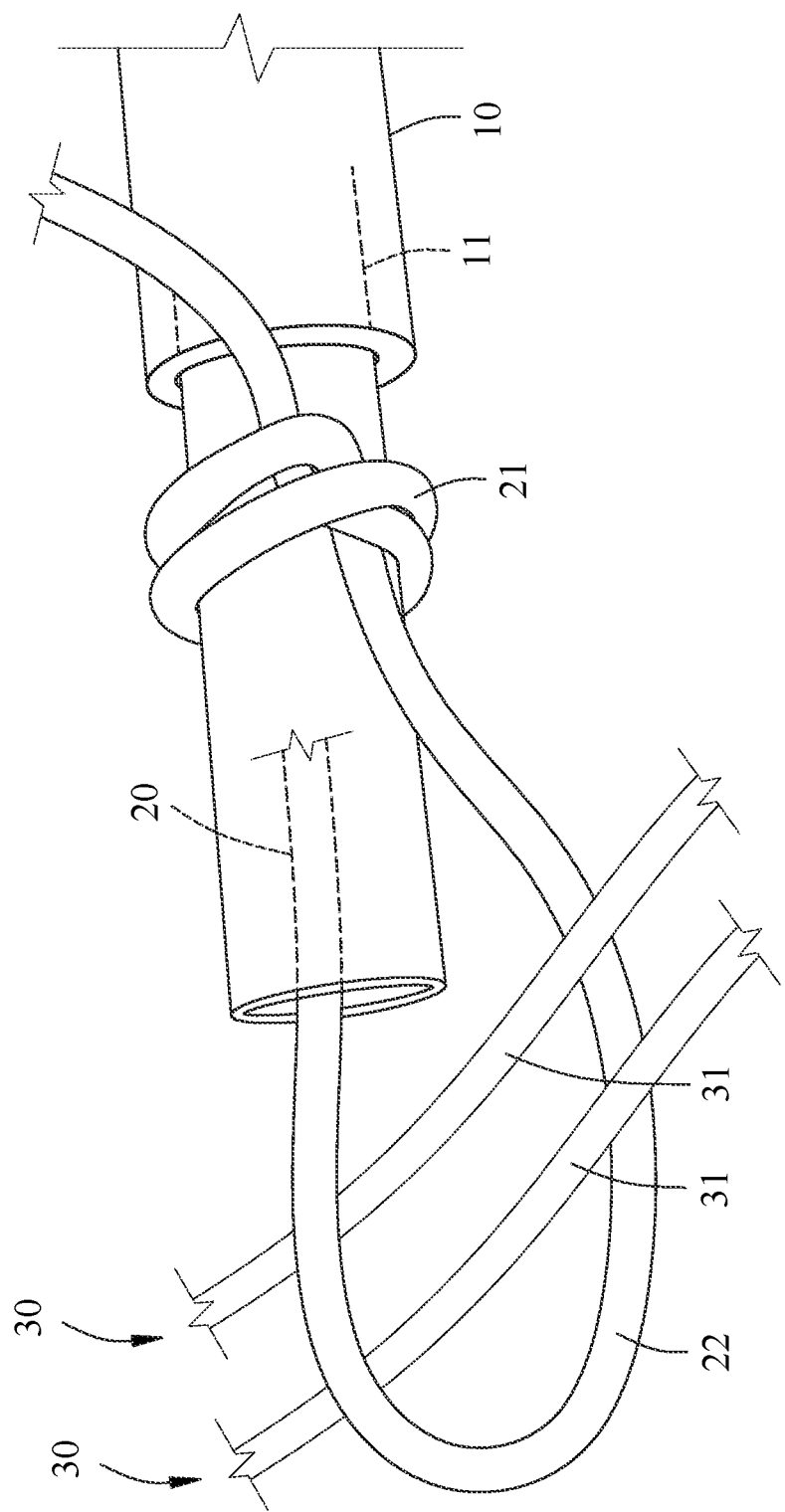
FIG. 5 is a perspective view of a second embodiment of a surgical knot assembly in accordance with the present disclosure.
Figure 6:
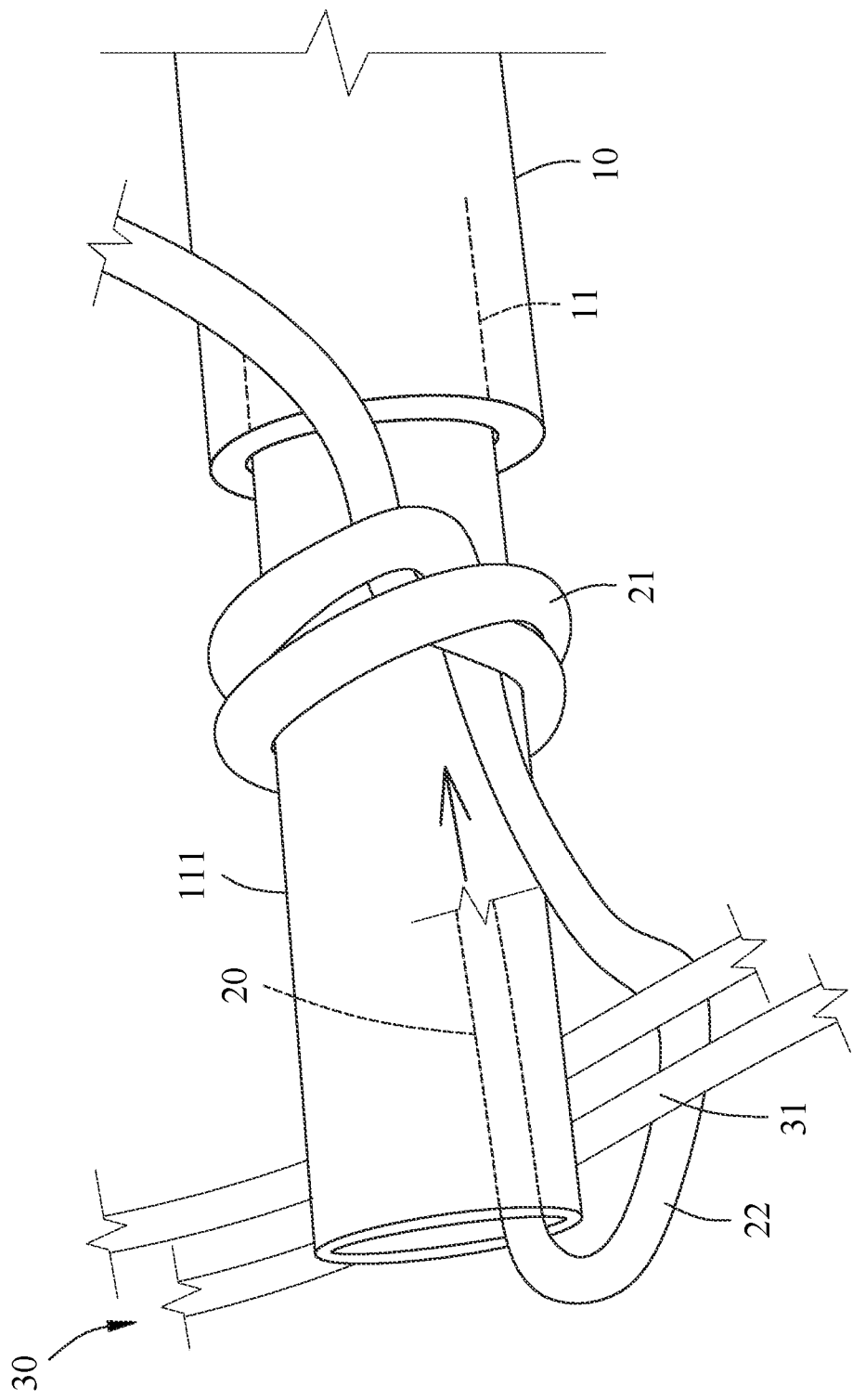
FIGS. 6 to 8 depicts the surgical knot assembly of FIG. 5 in operation.
Figure 7:
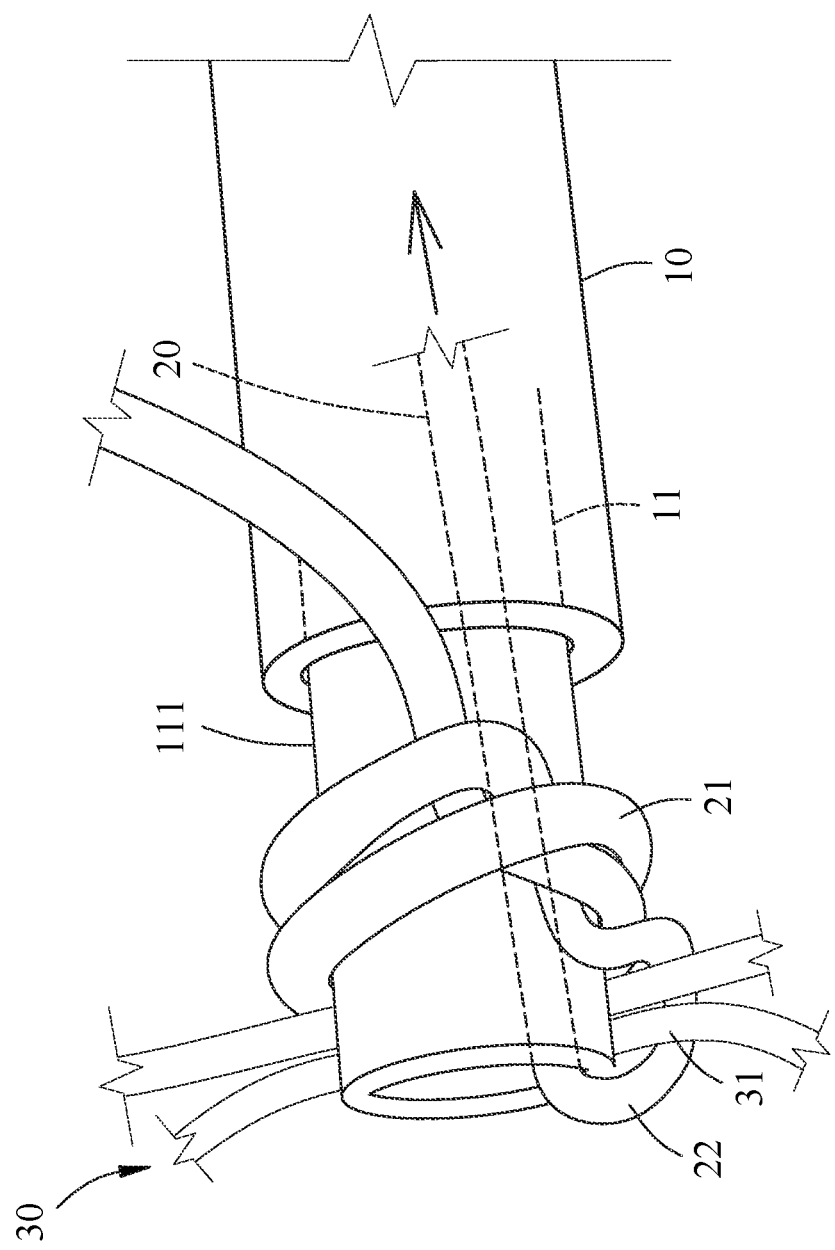
Figure 8:
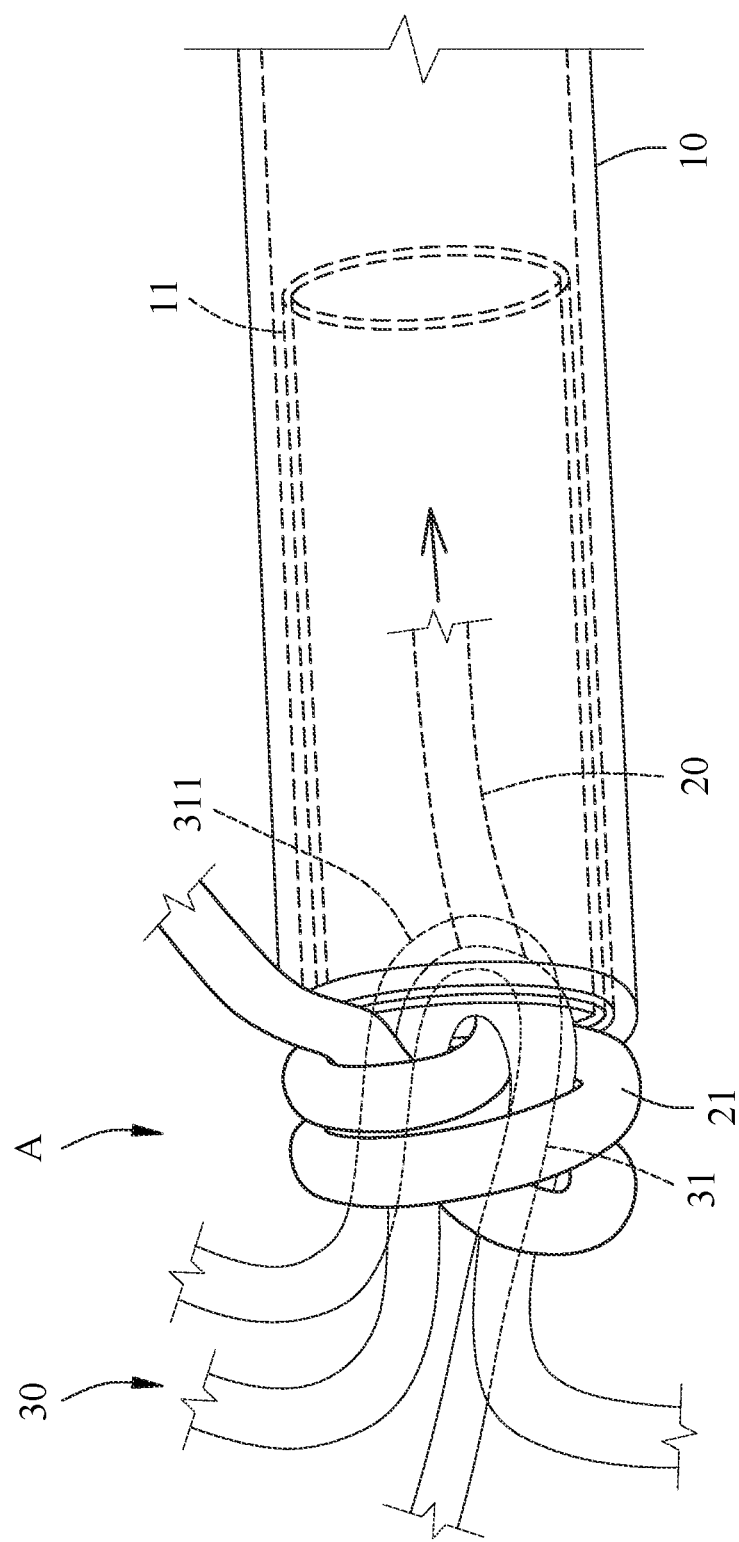

The relative position between the outer tube 10, the inner tube 11 and the pre-tied knot 21 is variable subject to the working and fastening of the suture filament 30 and can be fixed during the operation by the operator to ensure that the suturing and knot-tying process for a patient can be adequately tended. As the operator retracts the inner tube 11 and tightens the loop 22, the surgical knot A is partially created and identified at the tip of the cavity 112. Preferably, the cavity 112 has a smaller diameter measurement than the suture material 20, suture filament 30 and pre-tied knot fastened together, e.g., the partially created surgical knot A has a greater diameter in width than the cavity 112, as shown in FIG. 4. In some embodiments, the cavity 112 provides holding and limitation of movements for the partially created surgical knot A to prevent disengagement thereof before the surgical knot A is fully tightened.

Referring to FIGS. 5-8, in one of the preferred embodiments, the suture material 20 is manoeuvred via the control as to close the loop 22. The loop 22 receives two strands of suture filament 30 therein and fastened to create the surgical knot A. As the surgical knot A is tightly fastened, the overall widths of the suture material 20 and filaments 30 are reduced and further compressed for knot security engaging the cavity 112.

Figure 9:
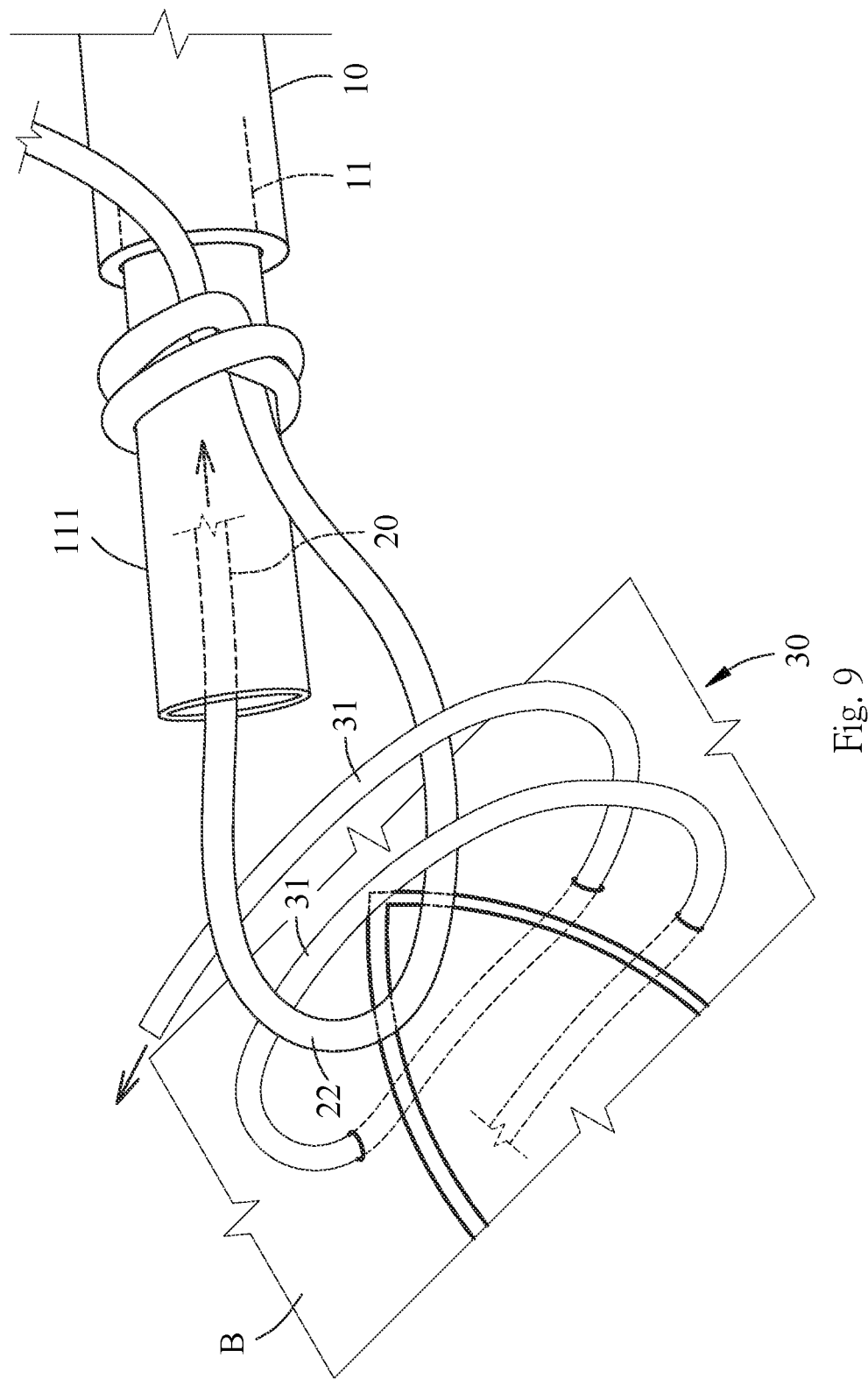
FIG. 9 is a perspective view of a third embodiment of a surgical knot assembly in accordance with the present disclosure.

In one embodiment, the suture filament 30 has a plurality of segments intertwined with the loop 22 before forming the surgical knot to obtain desired knot strength as shown in FIG. 9.

Figure 10:
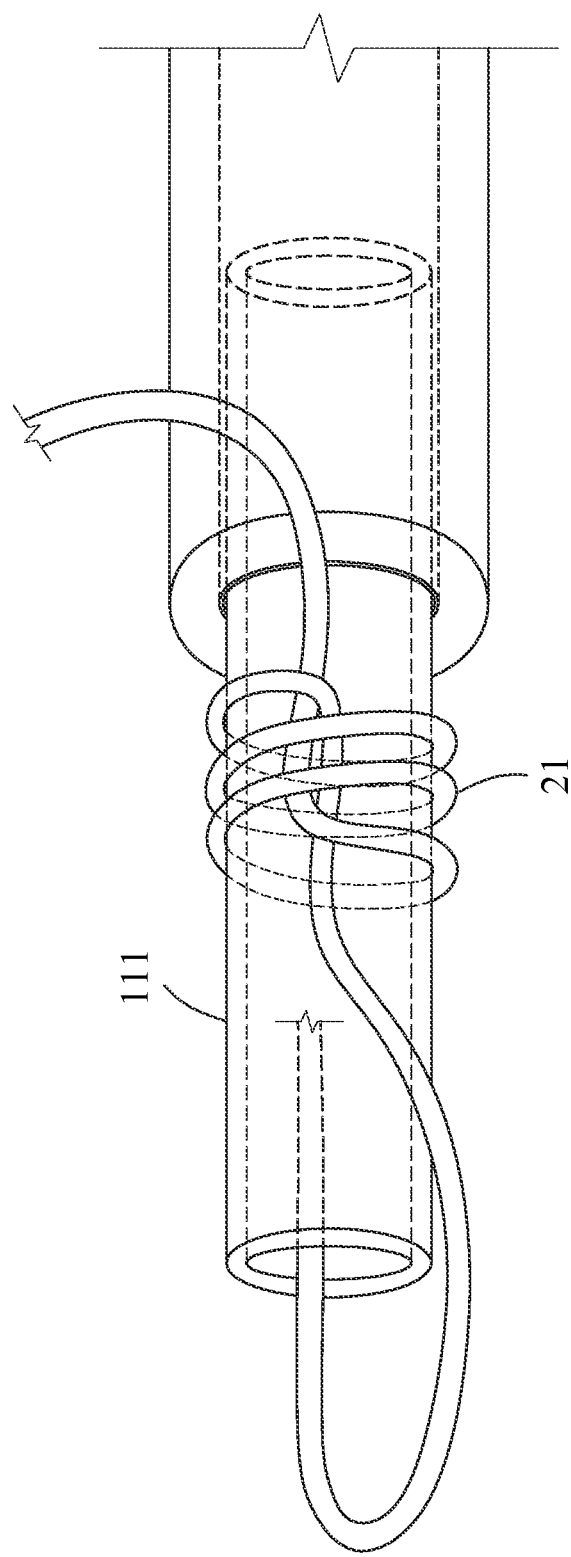
FIG. 10 is a perspective view of a fourth embodiment of a surgical knot assembly in accordance with the present disclosure.

In some embodiments, the pre-tied knot 21 is whirled multiple times around the inner tube 11, as shown in FIG. 10. The number of times that the pre-tied knot 21 is whirled around the inner tube 11 is subject to the suture material 20 used, number of strands of the filament 30 applied and the desired knot strength that the operator sees fit for the operation. There could be several ways of how the pre-tied knot is configured in conjunction with the usage of the assembly.

Although there are multiple different embodiments of the surgical knot assembly, but each of the applicable configuration and/or arrangement has its own merits to accommodate the relevant fittings for the operation. A maximum compression capacity of the suture material 20 and filament 30 is pre-determined with the selected combination of the surgical knot assembly. The operator selects and/or choose the preferred configuration of the assembly, then a corresponding pre-determined point as to how far the partially formed surgical knot could reach within inner tube 11 is set, such that once reached it would not slide any further into the cavity 112. The operator would perceive the tactile sense of tying the knot as tightened in light of the friction and resistance starts to develop and the knot abutting to the walls of the cavity 112 of the inner tube 11 tightly. This mechanism ensures the tightness of the created surgical knot is solid, but not jammed in the cavity 112 and is readily available for placement at the treatment site B.

Even though numerous characteristics and advantages of the present disclosure have been set forth in the foregoing description, together with details of the structures and functions thereof, the present disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A surgical knot assembly for tying a surgical knot, comprising:
   an outer tube;
   an inner tube slidably interconnected within the outer tube and having a distal end protruding from the outer tube as a neck; and
   a strand of suture material having a first portion of a length configured releasably engaged to the neck being a pre-tied knot, and having a second portion of a length extending from a cavity at the distal end of the inner tube, thereby forming a loop between the distal end of the inner tube and the neck, at least one strand of suture filament mounted through the loop,
   wherein size of the loop is variable by maneuvering the suture material and closing the loop as the neck retracts back into the outer tube, and wherein the loop, the pre-tied knot and the at least one strand of suture filament are fastened together creating a surgical knot held at the cavity.

2. The surgical knot assembly according to claim 1, wherein the cavity of the inner tube has a smaller diameter than a sum of a diameter of the loop, the pre-tied knot and the at least one strand of suture filament fastened together.

3. The surgical knot assembly according to claim 2, wherein the pre-tied knot is whirled around the inner tube fix at least one time and that the suture material and the at least one strand of suture filament having a same measurement and dimension.

4. The surgical knot assembly according to claim 3, wherein at least two strands of the suture filaments have plurality of segments intertwining with the loop.

5. The surgical knot assembly according to claim 4, wherein the at least one strand of suture filament is configured to first penetrate through a body tissue or a treatment site before intertwining with the loop.

6. The surgical knot assembly according to claim 2, wherein at least two strands of the suture filament intertwining the loop.

7. The surgical knot assembly according to claim 6, wherein the at least one strand of suture filament is configured to first penetrate through a body tissue or a treatment site before intertwining with the loop.

8. The surgical knot assembly according to claim 1, wherein the at least one strand of suture filament has a plurality of segments intertwining with the loop.

9. The surgical knot assembly according to claim 8, wherein the at least one strand of suture filament is configured to first penetrate through a body tissue or a treatment site before intertwining with the loop.

* * * * *